United States Patent
Kim et al.

(10) Patent No.: US 9,139,872 B2
(45) Date of Patent: Sep. 22, 2015

(54) METHOD AND APPARATUS FOR ANALYZING NUCLEIC ACID BY COMPENSATING FOR CROSSTALK IN POLYMERASE CHAIN REACTION DATA AND OTHER DATA

(71) Applicant: Samsung Electronics Co., Ltd., Suwon-si, Gyeonggi-do (KR)

(72) Inventors: Kyung-ho Kim, Seoul (KR); Soo-kwan Lee, Seoul (KR); Joon-ho Kim, Seongnam-si (KR); Kak Namkoong, Seoul (KR); Sun-ok Jung, Seongnam-si (KR); Won-seok Chung, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 122 days.

(21) Appl. No.: 13/754,628

(22) Filed: Jan. 30, 2013

(65) Prior Publication Data

US 2014/0005073 A1    Jan. 2, 2014

(30) Foreign Application Priority Data

Jun. 28, 2012 (KR) ........................ 10-2012-0070234

(51) Int. Cl.
*C12Q 1/68* (2006.01)

(52) U.S. Cl.
CPC .............. *C12Q 1/686* (2013.01); *C12Q 1/6848* (2013.01); *C12Q 1/68* (2013.01)

(58) Field of Classification Search
None
See application file for complete search history.

(56) References Cited

U.S. PATENT DOCUMENTS

| 7,209,836 | B1 | 4/2007 | Schermer et al. |
| 7,839,507 | B2 | 11/2010 | Gunstream et al. |
| 8,095,322 | B2 | 1/2012 | Kurnik et al. |
| 2009/0035779 | A1 | 2/2009 | Kurnik et al. |

FOREIGN PATENT DOCUMENTS

WO    WO 2011/031585 A1    3/2011

*Primary Examiner* — James Martinell
(74) *Attorney, Agent, or Firm* — Leydig, Voit & Mayer, Ltd.

(57) ABSTRACT

A method of analyzing nucleic acid by compensating for crosstalk in polymerase chain reaction (PCR) data and other data, wherein crosstalk signals associated with multiple fluorescent dyes are corrected by using fluorescent intensity variations detected from a concentration difference of the fluorescent dyes, and apparatus for performing the method.

9 Claims, 10 Drawing Sheets

| Crosstalk (%) | FAM | Cal Fluor 560 | Cal Fluor 610 | Quasar 670 |
|---|---|---|---|---|
| Blue channel | 100.0% | 3.0% | −0.1% | 0.2% |
| Green channel | 0.9% | 100.0% | 2.2% | 0.4% |
| Orange channel | −0.1% | 1.0% | 100.0% | 4.1% |
| Red channel | −0.1% | 0.0% | 1.2% | 100.0% |

FIG. 4A

< 2-plex FAM channel signal & Cross-tak signal >

FIG. 4B

< 2-plex Cal Fluor 560 channel signal & Cross-talk signal >

METHOD AND APPARATUS FOR ANALYZING NUCLEIC ACID BY COMPENSATING FOR CROSSTALK IN POLYMERASE CHAIN REACTION DATA AND OTHER DATA

CROSS-REFERENCE TO RELATED APPLICATION

This application claims the benefit of Korean Patent Application No. 10-2012-0070234, filed on Jun. 28, 2012, in the Korean Intellectual Property Office, the disclosure of which is incorporated herein in its entirety by reference.

BACKGROUND

1. Field

The present disclosure relates to methods and apparatuses for analyzing nucleic acid by compensating for crosstalk in polymerase chain reaction (PCR) data, microarray data, etc.

2. Description of the Related Art

Polymerase chain reaction (PCR) is currently used in almost all tests for manipulating a genetic material, and is a method of amplifying a certain target genetic material to be detected. Since a small amount of a genetic material having the same base sequence may be amplified to a large amount, PCR is used to diagnose various genetic diseases by amplifying nucleic acids such as deoxyribonucleic acid (DNA) of humans. Also, infectious diseases may be diagnosed by using PCR for nucleic acid of bacteria, viruses, or fungi.

In general, PCR includes three steps: performing denaturation to separate two strands of DNA by using heat, reducing temperature to anneal a primer to an end of a sequence to be amplified and slightly increasing temperature to cause polymerization or extension for synthesizing DNA. Since the amount of a genetic material is doubled by performing PCR once, if PCR is performed repeatedly, the amount of nucleic acid may be amplified geometrically.

Recently, multiplex PCR (real-time multiplex PCR) for amplifying multiple target genetic material by using different fluorescent dyes or probes has been introduced. In order to obtain a test result using multiplex PCR, filters for detecting certain wavelength bands of different colors of fluorescent light emitted from different fluorescent dyes are used. However, since these filters have adjacent wavelength bands, crosstalk may occur due to fluorescent signals of adjacent bands, and thus, an accurate test result may not be easily obtained. Accordingly, research is being conducted on how to perform accurate analysis of nucleic acid in consideration of crosstalk.

SUMMARY

Provided are methods and apparatuses for analyzing nucleic acid by compensating for crosstalk in polymerase chain reaction (PCR) data, microarray data, etc.

In one aspect, there is provided a nucleic acid analysis method comprising: obtaining (e.g., by detecting) a difference in concentration between different fluorescent dyes labeled on a nucleic acid by using (e.g., by measuring) a difference between fluorescent intensity variations detected from the fluorescent dyes; correcting crosstalk signals due to the fluorescent dyes by using the obtained (detected) difference in concentration; and estimating (calculating) final threshold cycles of the fluorescent dyes by compensating for the detected fluorescent intensity variations by using the corrected crosstalk signals.

Also provided is a non-transitory computer-readable recording media having recorded thereon a computer program for executing the method.

According to another aspect of the present invention, a nucleic acid analysis apparatus is provided, which includes a concentration analysis unit that obtains (e.g., by detecting) a difference in concentration between different fluorescent dyes labeled on a nucleic acid by using (e.g., by measuring) a difference between fluorescent intensity variations detected from the fluorescent dyes; a correction unit that corrects crosstalk signals due to the fluorescent dyes by using the obtained (detected) difference in concentration; and an estimation unit that estimates final threshold cycles of the fluorescent dyes by compensating for the detected fluorescent intensity variations by using the corrected crosstalk signals.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, expressions such as "at least one of," when preceding a list of elements, modify the entire list of elements and do not modify the individual elements of the list.

Figure 1:
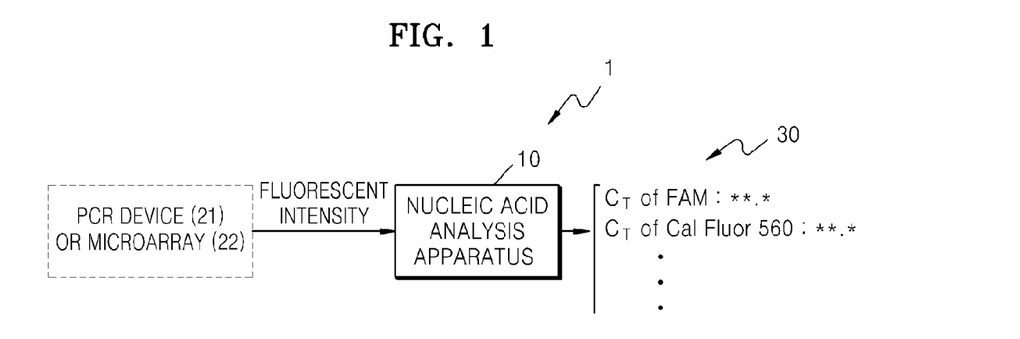
FIG. 1 is a block diagram of a nucleic acid analysis system.

FIG. 1 is a block diagram of a nucleic acid analysis system 1 according to an embodiment of the present invention. Referring to FIG. 1, the nucleic acid analysis system 1 includes a polymerase chain reaction (PCR) device 21 or a microarray 22, and a nucleic acid analysis apparatus 10. In the nucleic acid analysis system 1 illustrated in FIG. 1, only components related to the current embodiment are illustrated to clearly show the features of the current embodiment. However, general-use components other than the components illustrated in FIG. 1 may be further included.

The nucleic acid analysis system 1 is a system for analyzing by using the nucleic acid analysis apparatus 10 a plurality of fluorescent signals detected from different fluorescent dyes labeled on a nucleic acid sample by the PCR device 21 or the microarray 22. As a result, quantitative analysis information 30 of nucleic acid is generated.

From among various analysis methods of detecting nucleic acid from a deoxyribonucleic acid (DNA) sample and quantitating the nucleic acid, a PCR (a real-time multiplex PCR) is one of the most commonly used methods and is well known to one of ordinary skill in the art.

The PCR device 21 is a device for exponentially amplifying a nucleic acid by performing three steps: performing denaturation to separate two strands of DNA by using heat, reducing temperature to anneal a primer to an end of a sequence to be amplified, and slightly increasing temperature again to cause polymerization or extension for synthesizing DNA. In particular, the PCR device 21 uses real-time PCR for quantitative analysis of a nucleic acid by detecting in real time the intensity of a fluorescent signal that is proportional to the concentration of the amplified nucleic acid.

Currently, real-time multiplex PCR for amplifying a target genetic material by using different fluorescent dyes is also used in many instances. In order to obtain a test result using a multiplex PCR, filters for detecting a certain wavelength band of each of different colors of fluorescent light emitted from different fluorescent dyes.

Figure 3A:
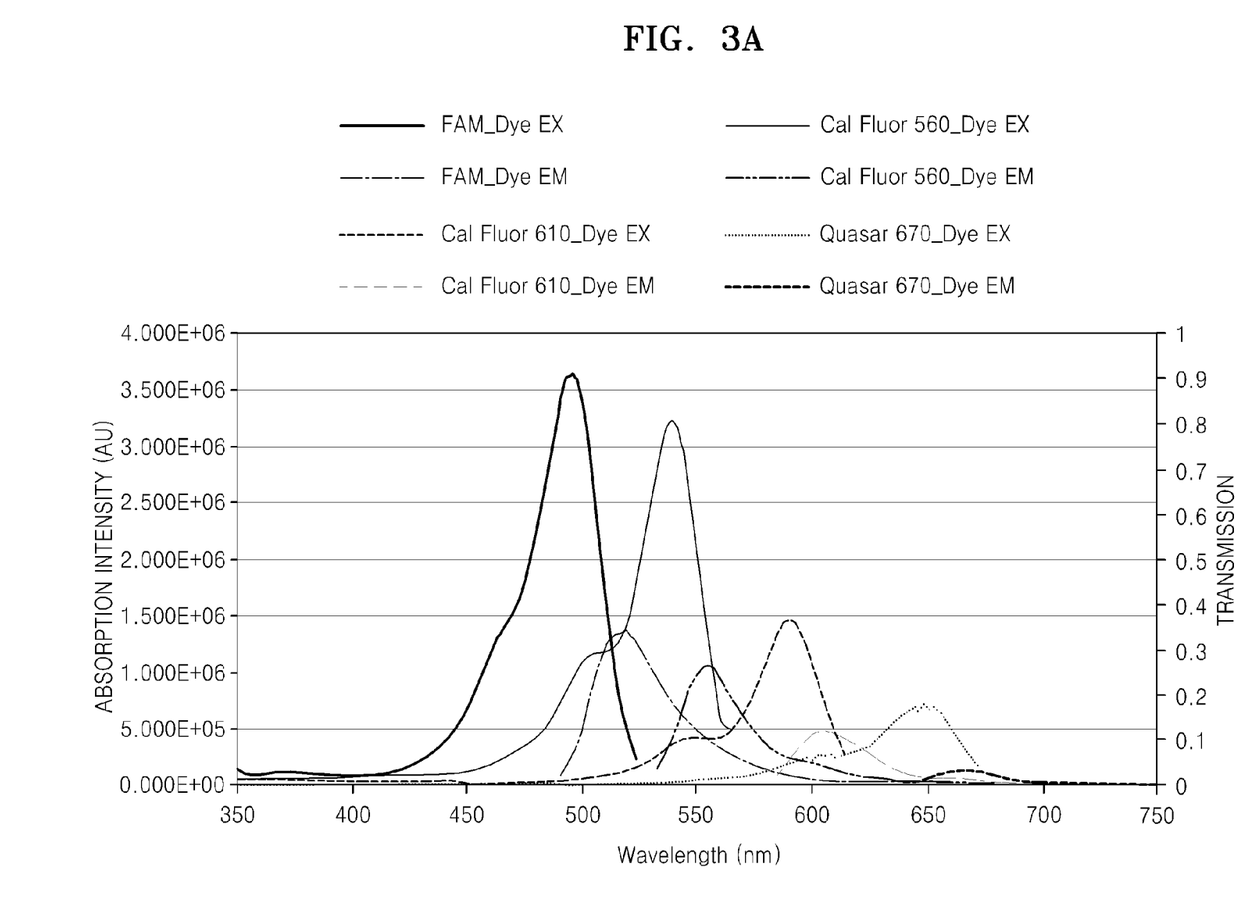
FIG. 3A is a graph showing spectra of fluorescent signals detected by using multiplex polymerase chain reaction (PCR) using fluorescent dyes of four colors.

FIG. 3A is a graph showing spectra of fluorescent signals detected by using multiplex PCR using four colors of fluorescent dyes. FIG. 3A shows spectra regarding FAM dye, Cal Fluor 560 dye, Cal Fluor 610 dye, and Quasar 670 dye. However, these spectra regarding the fluorescent dyes may have adjacent wavelength bands and crosstalk may occur due to fluorescent signals of the adjacent bands. Crosstalk is the influence that the fluorescence of one fluorescent dye has on the detection of a different fluorescent dye due to overlap of the emission spectra of the dyes. In particular, if multiplex PCR uses a large number of colors of fluorescent dyes, since overlapping spectra increase, more crosstalk may occur.

Figure 3B:
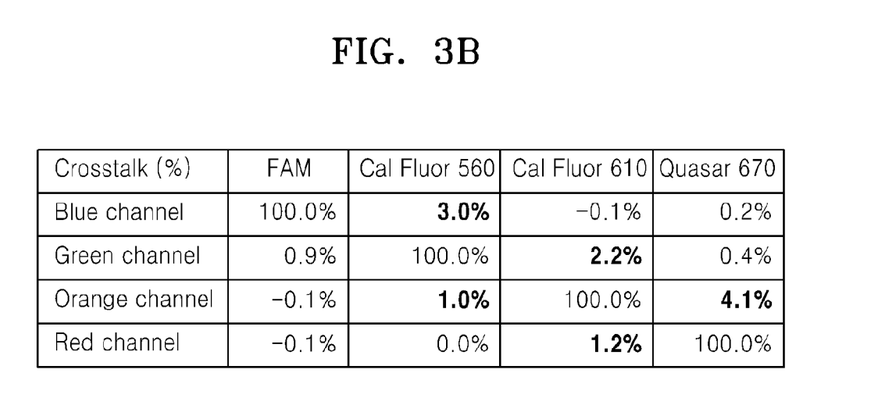
FIG. 3B is a table showing crosstalk between dyes.

FIG. 3B is a table showing crosstalk between dyes. Referring to FIG. 3B, each of FAM dye, Cal Fluor 560 dye, Cal Fluor 610 dye, and Quasar 670 dye corresponds to a blue channel, a green channel, an orange channel, and a red channel, and values in the table are obtained by optimally designing fluorescent filters (excitation, emission, dichroic filter) to minimize crosstalk. For example, a fluorescent signal regarding FAM dye has crosstalk of 3.0% due to Cal Fluor 560 dye, −0.1% due to Cal Fluor 610 dye, and 0.2% due to Quasar 670 dye. Also, fluorescent signals regarding Cal Fluor 560 dye, Cal Fluor 610 dye, and Quasar 670 dye may have crosstalk as shown in FIG. 3B.

As described above, even when fluorescent filter bands are optimally designed to minimize crosstalk, since fluorescent signals regarding fluorescent dyes interfere with each other due to the crosstalk, if the number of colors of fluorescent light to be detected is increased, a test result, e.g., a result of quantitating nucleic acid, may not be accurately obtained. Accordingly, an analysis result of nucleic acid needs to be accurately analyzed in consideration of crosstalk.

Typical multiplex PCR using a plurality of fluorescent dyes has been suggested in consideration of crosstalk between detected fluorescent signals. However, the crosstalk is considered regardless of the difference in concentration between fluorescent dyes on the assumption that the fluorescent dyes have the same concentration.

In actuality, however, in multiplex PCR, fluorescent dyes may have different concentrations intentionally or unintentionally. Since a fluorescent dye having a high concentration may have much crosstalk due to other fluorescent dyes, in order to accurately obtain an analysis result of nucleic acid, crosstalk has to be reflected in consideration of the concentrations of fluorescent dyes.

Accordingly, the nucleic acid analysis apparatus 10 of the nucleic acid analysis system 1 is an apparatus capable of obtaining a more accurate result of analyzing nucleic acid by reflecting crosstalk in consideration of concentrations of fluorescent dyes when a plurality of fluorescent dyes are simultaneously used by the PCR device 21 or the microarray 22.

The PCR device 21 of the nucleic acid analysis system 1 may be a device for performing multiplex PCR, and the microarray 22 may be a device using different fluorescent dyes in every spot. Also, a microfluidic device using different fluorescent dyes in one chamber may be used instead of the PCR device 21 or the microarray 22.

That is, it would be understood by one of ordinary skill in the art that the nucleic acid analysis system 1 may use any device other than the PCR device 21 or the microarray 22 as long as the device detects fluorescent signals from different fluorescent dyes labeled on nucleic acid. Although the structure and operation of the nucleic acid analysis apparatus 10 will be described below on the assumption that the PCR device 21 for performing multiplex PCR is used, it would be understood by one of ordinary skill in the art that the nucleic acid analysis apparatus 10 is not limited thereto.

Figure 2:
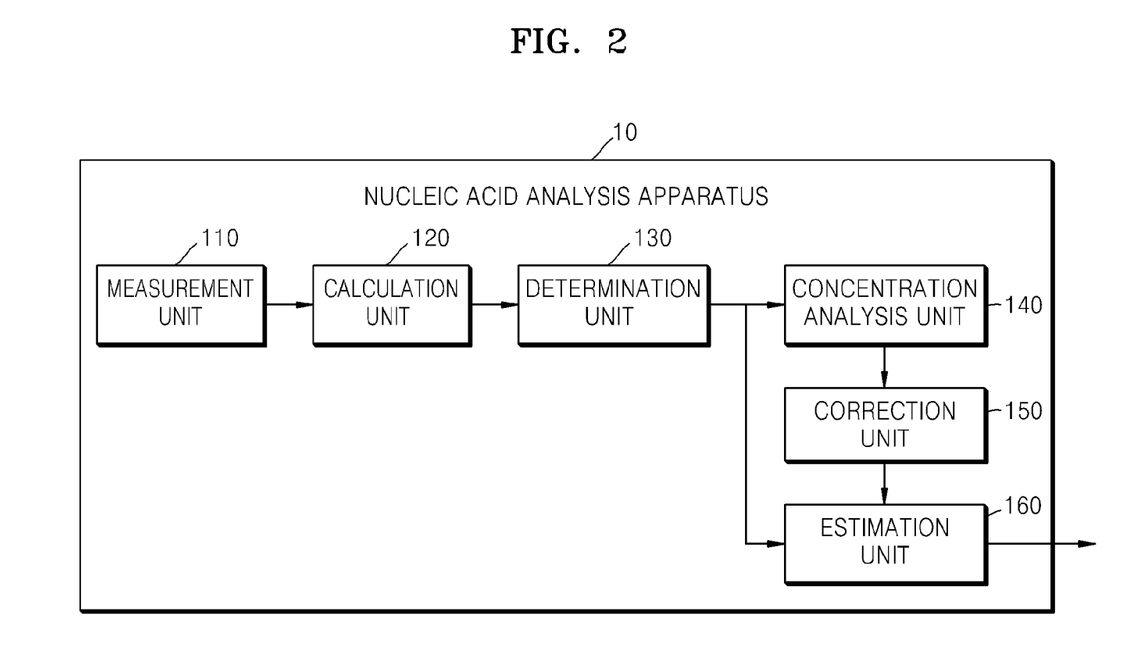
FIG. 2 is a block diagram of a nucleic acid analysis apparatus.

FIG. 2 is a block diagram of the nucleic acid analysis apparatus 10 according to an embodiment of the present invention. Referring to FIG. 2, the nucleic acid analysis apparatus 10 includes a measurement unit 110, a calculation unit 120, a determination unit 130, a concentration analysis unit 140, a correction unit 150, and an estimation unit 160. In FIG. 2, only hardware components related to the current embodiment are illustrated to clearly show the features of the current embodiment. However, it would be understood by one of ordinary skill in the art that the nucleic acid analysis apparatus 10 may further include general-use hardware components other than the hardware components illustrated in FIG. 2.

In particular, the nucleic acid analysis apparatus 10 illustrated in FIG. 2 may be driven by a processor. The processor may include an array of a plurality of logic gates, or may include a combination of a general-use microprocessor and memory that stores a program executable in the microprocessor. Also, it would be understood by one of ordinary skill in the art that the nucleic acid analysis apparatus 10 may further include general hardwares other than the processor.

The measurement unit 110 receives a result of detecting colors of fluorescent light emitted form different fluorescent dyes labeled on nucleic acid by the PCR device 21 or the microarray 22, and measures fluorescent intensity variations. A process of measuring the fluorescent intensity variations according to fluorescent signals output from the PCR device 21 or the microarray 22 is well known to one of ordinary skill in the art, and thus a detailed description thereof is not provided here.

Meanwhile, it is described above in relation to FIG. 1 that the PCR device 21 or the microarray 22 is a device using different fluorescent dyes. However, before a plurality of fluorescent dyes are simultaneously used in multiplex PCR, the nucleic acid analysis apparatus 10 previously receives fluorescent signals generated when the fluorescent dyes are individually used, and stores calibration information regarding crosstalk in a storage (not shown). A detailed description thereof will now be provided with reference to FIGS. 4A and 4B.

Figure 4A:
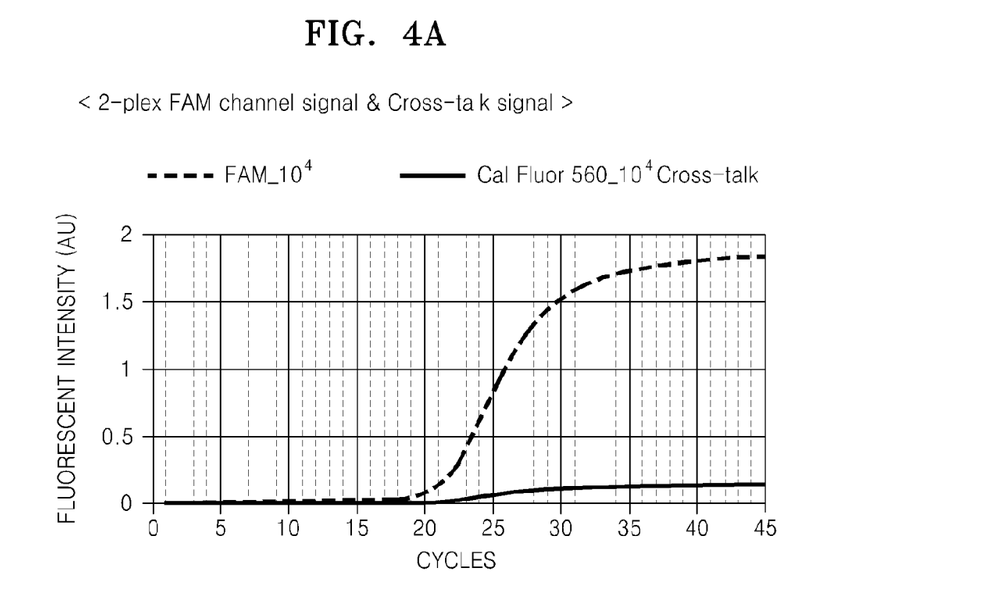
FIG. 4A is a graph showing fluorescent intensity variations and crosstalk measured by a measurement unit with respect to FAM dye in 2-plex PCR.

FIG. 4A is a graph showing fluorescent intensity variations and crosstalk measured by the measurement unit 110 with respect to FAM dye in 2-plex PCR, according to an embodiment of the present invention. Referring to FIG. 4A, on the assumption that FAM dye and Cal Fluor 560 dye have the same concentration, fluorescent intensity variations regarding FAM dye, and crosstalk due to Cal Fluor 560 dye are shown. In the following description, the concentration of FAM dye and Cal Fluor 560 dye, i.e., $10^4$, corresponds to a relative indicator.

Figure 4B:
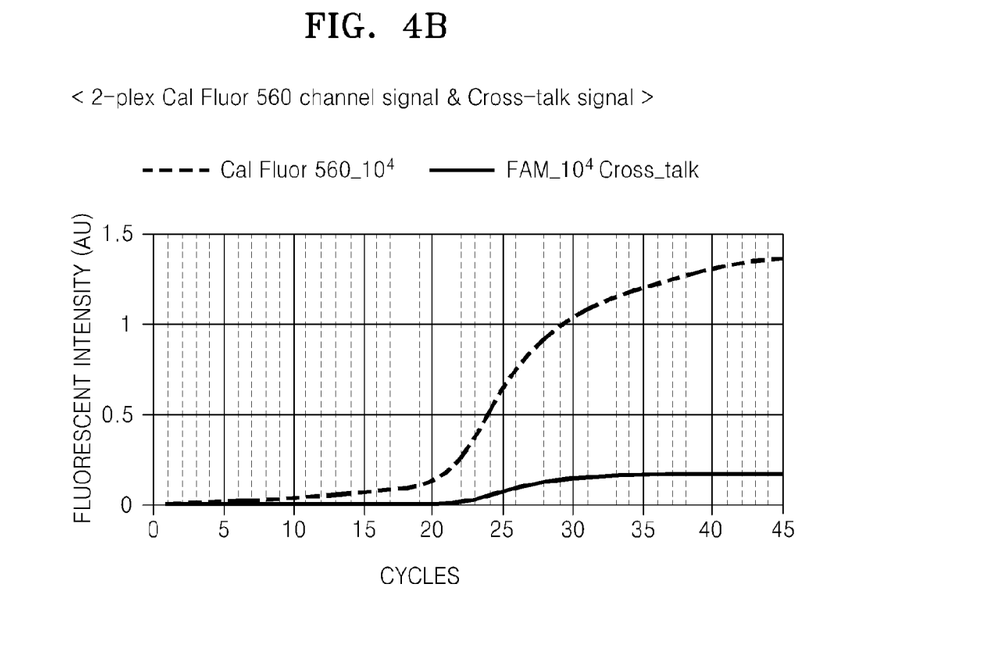
FIG. 4B is a graph showing fluorescent intensity variations and crosstalk measured by the measurement unit with respect to Cal Fluor 560 dye in 2-plex PCR.

FIG. 4B is a graph showing fluorescent intensity variations and crosstalk measured by the measurement unit 110 with respect to Cal Fluor 560 dye in 2-plex PCR, according to an embodiment of the present invention. Referring to FIG. 4B, as a case opposite to the case illustrated in FIG. 4A, fluorescent intensity variations regarding Cal Fluor 560 dye and crosstalk due to FAM dye are shown on the assumption that Cal Fluor 560 dye and FAM dye have the same concentration.

Referring to FIGS. 4A and 4B, when FAM dye and Cal Fluor 560 dye having the same concentration are used in 2-plex PCR, a correction coefficient $a_{12}$ indicating crosstalk due to Cal Fluor 560 dye and a correction coefficient $a_{21}$ indicating crosstalk due to FAM dye may be defined by using Equation 1.

[Equation 1]

$$a12 = \frac{\text{average (five points plateau of Cal560\_cross-talk)}}{\text{average(five points plateau of FAM\_}10^4)}$$

$$a21 = \frac{\text{average(five points plateau of FAM\_cross-talk)}}{\text{average(five points plateau of Cal560\_}10^4)}$$

According to FIGS. 4A and 4B, and Equation 1, when 2-plex PCR is performed on FAM dye, the correction coefficient $a_{12}$ indicating crosstalk due to Cal Fluor 560 dye may be calculated as 0.03685. When 2-plex PCR is performed on Cal Fluor 560 dye, the correction coefficient $a_{21}$ indicating crosstalk due to FAM dye may be calculated as 0.13568.

Five points plateau refers to values (fluorescence intensities) of five arbitrary points in a graph of FIG. 4A or 4B. $a_{12}$=0.03685 and $a_{21}$=0.13568 are simulation values in the simulation graph of FIG. 4A or 4B.

The nucleic acid analysis apparatus 10 may previously store in a storage (not shown) results of performing single-plex PCR on each of the fluorescent dyes as calibration information.

Referring back to FIG. 2, the measurement unit 110 measures fluorescent intensity variations according to fluorescent signals output from the PCR device 21 that performs 2-plex PCR. That is, if 2-plex PCR is performed, the measurement unit 110 measures fluorescent intensity variations with respect to FAM dye and Cal Fluor 560 dye.

Although 2-plex PCR using FAM dye and Cal Fluor 560 dye is representatively described below for convenience of explanation, it would be understood by one of ordinary skill in the art that the same principle may also be applied to 3-plex PCR, 4-plex PCR, 5-plex PCR, 6-plex PCR, etc.

Figure 5:
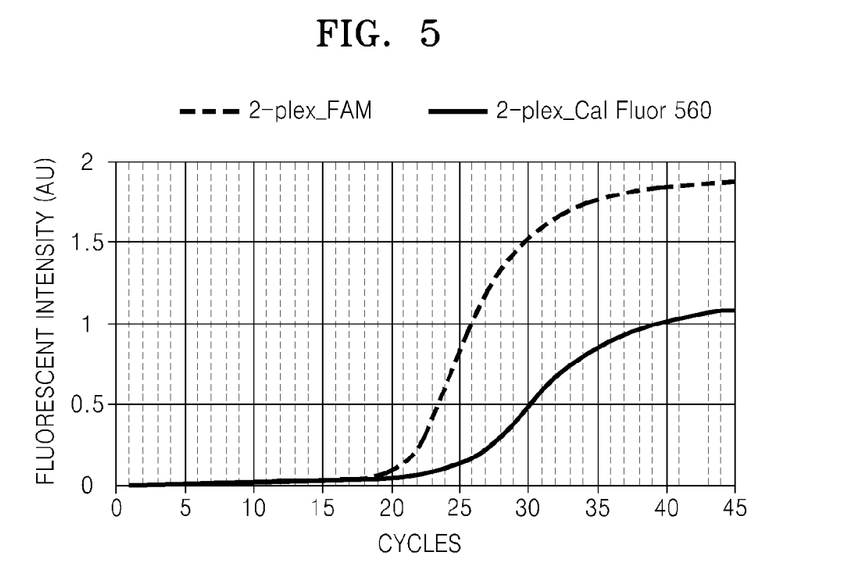
FIG. 5 is a graph showing fluorescent intensity variations measured by the measurement unit with respect to FAM dye and Cal Fluor 560 dye in 2-plex PCR.

FIG. 5 is a graph showing fluorescent intensity variations measured by the measurement unit 110 with respect to FAM dye and Cal Fluor 560 dye in 2-plex PCR, according to an embodiment of the present invention. Referring to FIG. 5, fluorescent intensity variations measured by the measurement unit 110 with respect to each of the fluorescent dyes may form a sigmoidal curve.

The curves shown in FIG. 5 are obtained under conditions that the concentration of FAM dye is $10^4$, the concentration of Cal Fluor 560 dye is $10^2$, crosstalk of Cal Fluor 560 dye with respect to FAM dye is 5%, and crosstalk of FAM dye with respect to Cal Fluor 560 dye is 10%. That is, FAM dye and Cal Fluor 560 dye used in multiplex PCR (2-plex PCR) have different concentrations.

Referring back to FIG. 2, the calculation unit 120 calculates initial threshold cycles (initial $C_T$s) of the fluorescent dyes by using the fluorescent intensity variations.

Generally, a threshold cycle $C_T$ corresponds to a value used to quantitate nucleic acid, e.g., to analyze an initial concentration of nucleic acid. The threshold cycle $C_T$ may be defined as a certain cycle number on a sigmoidal curve obtained as a result of PCR. The threshold cycle $C_T$ may be calculated by arbitrarily setting a threshold line parallel to an x axis, and determining the threshold cycle $C_T$ as an x-axis value that crosses (intersects) the sigmoidal curve of fluorescent intensity. It also includes first-order or second-order differentiation for determining the threshold cycle $C_T$ as a maximum value of a first-order or second-order differentiation curve of a sigmoidal curve. The threshold cycle $C_T$ is well known to one of ordinary skill in the art, and thus a detailed description thereof is not provided here.

Figure 6:
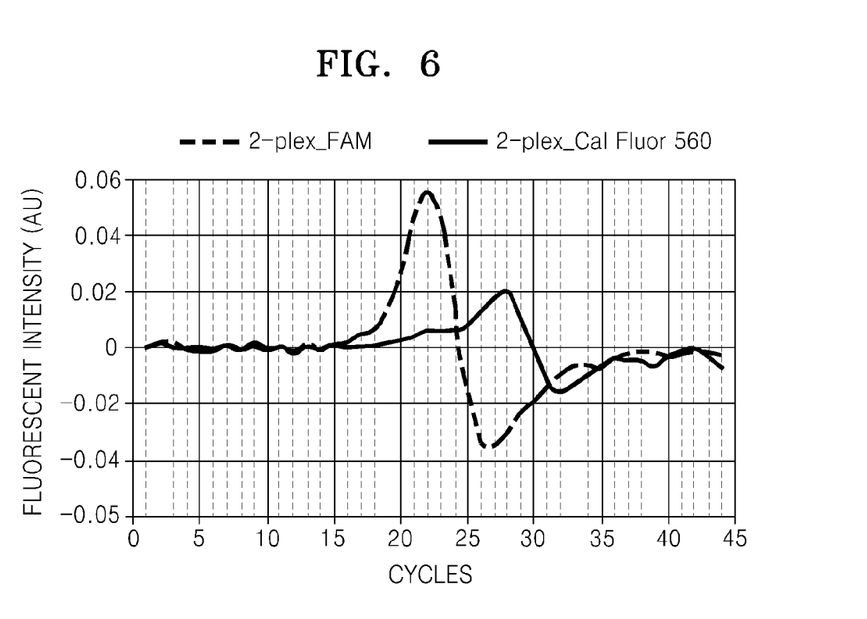
FIG. 6 is a graph showing a process of calculating initial threshold cycles in a calculation unit.

FIG. 6 is a graph showing a process of calculating the initial $C_T$s in the calculation unit 120, according to an embodiment of the present invention. Curves shown in FIG. 6 are results of differentiating the fluorescent intensity variation curve regarding FAM dye and the fluorescent intensity variation curve regarding Cal Fluor 560 dye, which are shown in FIG. 5, by using second-order differentiation.

The calculation unit 120 calculates a cycle number corresponding to a peak value of the differentiation curve regarding FAM dye as an initial threshold cycle regarding FAM dye (initial $C_{T\_}$FAM), and also calculates a cycle number corresponding to a peak value of the differentiation curve regarding Cal Fluor 560 dye as an initial threshold cycle regarding Cal Fluor 560 dye (initial $C_{T\_}$Cal Fluor 560). As shown in FIG. 5, since the concentration of FAM dye is higher than the concentration of Cal Fluor 560 dye, a peak is shown first on the differentiation curve regarding FAM dye.

According to the graph shown in FIG. 6, the calculation unit 120 calculates the initial $C_{T\_}$FAM as 22.03 and also calculates the initial $C_{T\_}$Cal Fluor 560 as 27.74 by performing second-order differentiation on the fluorescent intensity variation curves shown in FIG. 5.

Different values are calculated as the initial $C_T\_FAM$ and the initial $C_T\_Cal\ Fluor\ 560$ by the calculation unit 120 because FAM dye and Cal Fluor 560 dye have different concentrations.

Referring back to FIG. 2, the determination unit 130 determines whether the initial $C_T$s of the fluorescent dyes are the same. That is, the determination unit 130 determines whether the initial $C_T\_FAM$ and the initial $C_T\_Cal\ Fluor\ 560$ are the same.

Differently from the above description, if the initial $C_T\_FAM$ and the initial $C_T\_Cal\ Fluor\ 560$ are the same, the estimation unit 160 directly estimates final threshold cycles (final $C_T$s). That is, in this case, the estimation unit 160 compensates for the initial $C_T\_FAM$ and the initial $C_T\_Cal\ Fluor\ 560$ by using crosstalk signals previously stored and obtained when the fluorescent dyes are individually used, and estimates the final $C_T$s of the fluorescent dyes. Here, the crosstalk signals obtained when the fluorescent dyes are individually used correspond to the above-described calibration information previously stored in the storage. Crosstalk signals include various information and can be a value (e.g., coefficient), a graph, etc., but is not limited thereto.

For example, if the determination unit 130 determines that the initial $C_T$s are the same, the estimation unit 160 may estimate the final $C_T$s by using Equation 2.

$$S_1 = (B_1 - a_{12}B_2)/(1 - a_{12} \cdot a_{21})$$

$$S_2 = (B_2 - a_{21}B_1)/(1 - a_{12} \cdot a_{21})$$ [Equation 2]

Referring to Equation 2, $S_1$ refers to a corrected signal of a first dye, $S_2$ refers to a corrected signal of a second dye, $B_1$ refers to an uncorrected signal of the first dye, $B_2$ refers to an uncorrected signal of the second dye, $a_{12}$ refers to a correction coefficient for correcting crosstalk due to the second dye, and $a_{21}$ refers to a correction coefficient for correcting crosstalk due to the first dye.

However, if the determination unit 130 determines that the initial $C_T\_FAM$ and the initial $C_T\_Cal\ Fluor\ 560$ are not the same, the nucleic acid analysis apparatus 10 considers the difference in concentration between FAM dye and Cal Fluor 560 dye.

The concentration analysis unit 140 obtains the difference in concentration between the fluorescent dyes by using the difference between fluorescent intensity variation curves. That is, the concentration analysis unit 140 obtains the difference in concentration between FAM dye and Cal Fluor 560 dye by using the difference between the initial $C_T\_FAM$ and the initial $C_T\_Cal\ Fluor\ 560$.

The concentration analysis unit 140 may obtain the difference in concentration by using Equation 3.

$$[\Delta n] = (1+E)^{\Delta C_T}$$ [Equation 3]

Referring to Equation 3, $\Delta n$ refers to the difference in concentration between fluorescent dyes, E refers to an amplification efficiency of PCR, and $\Delta C_T$ refers to the difference between initial threshold cycles.

According to the above-described example of FIGS. 5 and 6, $\Delta C_T$ is 5.71. If the amplification efficiency E of PCR is 1, the difference $\Delta n$ in concentrations of FAM dye and Cal Fluor 560 dye is calculated as 52.35. As such, the concentration analysis unit 140 obtains the difference $\Delta n$ in concentrations of FAM dye and Cal Fluor 560 dye as 52.35.

The correction unit 150 corrects the crosstalk signals due to the fluorescent dyes by using the obtained difference in concentration. Here, the corrected crosstalk signals are signals corrected by reflecting the difference in concentration obtained by the concentration analysis unit 140 to the crosstalk signals previously stored and obtained when the fluorescent dyes are individually used.

In more detail, the correction unit 150 adjusts the fluorescent intensity variation curves of the crosstalk signals due to the fluorescent dyes by using the difference in concentration obtained by the concentration analysis unit 140, thereby correcting the crosstalk signals. After that, the correction unit 150 readjusts the adjusted result by using the difference between initial threshold cycles of the fluorescent dyes, thereby correcting the crosstalk signals.

Initially, the correction unit 150 corrects fluorescent intensities of the fluorescent dyes by using Equation 4.

$$I_F = I_0 \cdot QY \cdot (1 - e^{-2.303 \cdot \epsilon \cdot c \cdot L}) \cdot k$$

$$I_{\Delta F} = (1 - e^{-2.303 \cdot c1})/(1 - e^{-2.303 \cdot c2})$$ [Equation 4]

QY: Fluorescence quantum yield
$\epsilon$: Molar extinction coefficient of fluorescence at $\lambda_{EX}$
c: Fluorescence concentration
L: Optical path length for excitation
$I_0$: Excitation source intensity at $\lambda_{EX}$
k: Fluorescence collection efficiency Referring to Equation 4, $I_{\Delta F}$ corresponds to a fluorescent intensity correction value, $I_F$ corresponds to a fluorescent intensity, c1 corresponds to a fluorescence concentration of FAM dye, and c2 corresponds to a fluorescence concentration of Cal Fluor 560 dye.

According to the above-described example of FIGS. 5 and 6, the difference $\Delta n$ in concentrations of FAM dye and Cal Fluor 560 dye, which is obtained by the concentration analysis unit 140, is 52.35. Accordingly, the correction unit 150 calculates $I_{\Delta F} = (1 - e^{-2.303 \cdot 52.35})/(1 - e^{-2.303 \cdot 1}) = 1/0.900 = 1.11$ by using Equation 4. The values of 52.35 and 1 for c1 and c2, respectively, were assigned for convenience of calculation. Accordingly, the obtained real value of c1 (FAM dye) or c2 (Cal Fluor 560 dye) may differ from the assigned values.

After that, the correction unit 150 corrects the fluorescent intensity variation curves regarding FAM dye and Cal Fluor 560 dye.

A process whereby the correction unit 150 corrects the fluorescent intensity variation curve regarding Cal Fluor 560 dye is as described below. The correction unit 150 corrects the crosstalk signal due to FAM dye by using Equation 5, and then corrects the fluorescent intensity variation curve regarding Cal Fluor 560 dye by using Equation 6.

FAM_corrected flu. intensity = 2plex · $a_{21}$ · $I_{\Delta F}$

FAM_corrected con. = FAM_corrected flu. intensity − $\Delta C_T$ [Equation 5]

Cal560_corrected = 2plex − FAM_corrected con. [Equation 6]

Referring to Equation 5, "2plex" corresponds to FAM dye & Cal 560 dye, and "FAM_corrected con." corresponds to a cross-talk signal by concentration-corrected FAM dye. Each value corresponds to a graph regarding fluorescent intensities of FAM dye. "Cal560_corrected" corresponds to a result of correcting a fluorescent intensity variation curve regarding Cal Fluor 560 dye.

Figure 7A:
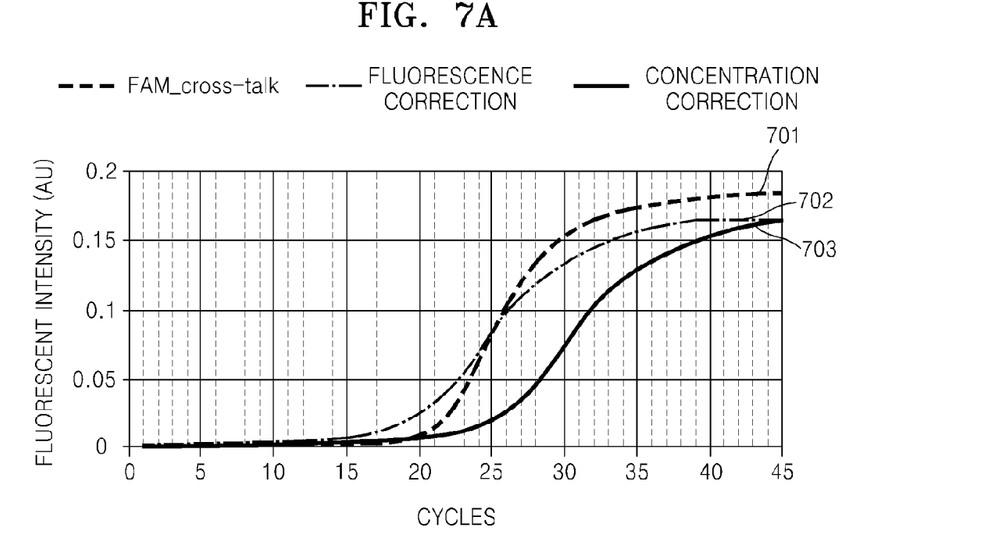
FIG. 7A is a graph showing a result of correcting a crosstalk signal due to FAM dye in a correction unit.

FIG. 7A is a graph showing a result of correcting a crosstalk signal due to FAM dye in the correction unit 150, according to an embodiment of the present invention. Referring to FIG. 7A, a cross-talk signal by FAM dye is (1) correcting Flu. Intensity→(2) correcting concentration. In particular, when referring to FIG. 7A, the fluorescent intensity of an original crosstalk signal 701 due to FAM dye is corrected by the correction unit 150 by using Equation 5, and thus, the original crosstalk signal 701 is changed into a fluorescence-corrected crosstalk signal 702. After that, the concentration of the fluorescence-corrected crosstalk signal 702 is corrected by the correction unit 150 by using Equation 6 and thus the fluorescence-corrected crosstalk signal 702 is changed into a concentration-corrected crosstalk signal 703.

Figure 7B:
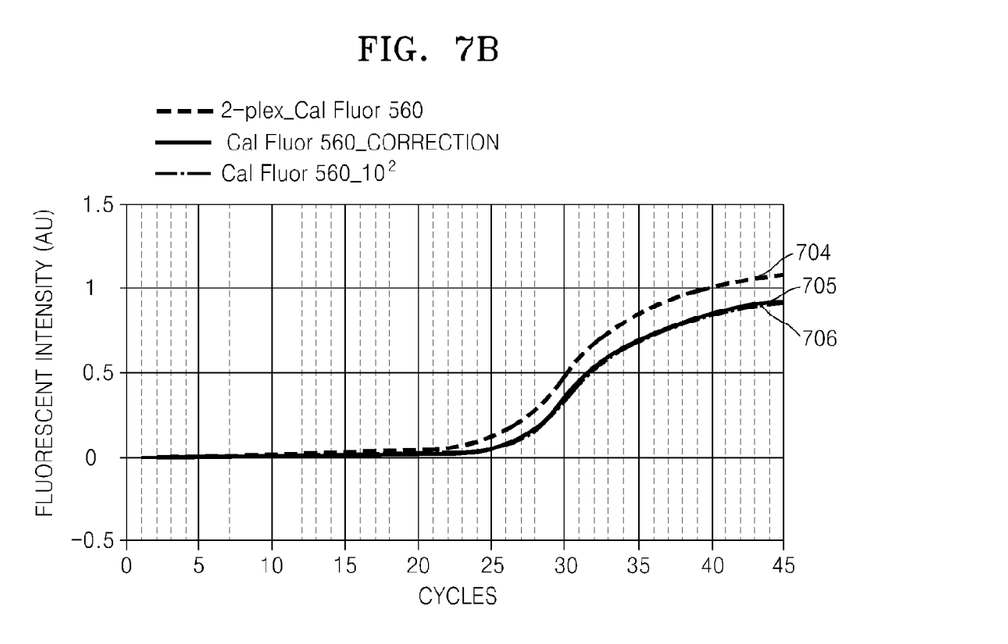
FIG. 7B is a graph showing a result of correcting a fluorescent intensity variation curve regarding Cal Fluor 560 dye in the correction unit.

FIG. 7B is a graph showing a result of correcting a fluorescent intensity variation curve regarding Cal Fluor 560 dye in the correction unit 150, according to an embodiment of the present invention. Referring to FIG. 7B, an original fluorescent intensity variation curve 704 regarding Cal Fluor 560 dye is compensated for by using the corrected crosstalk signal 703 shown in FIG. 7A, and thus, is changed into a corrected variation curve 705.

As such, the corrected variation curve 705 is hardly different from an actual variation curve 706 regarding Cal Fluor 560 dye. That is, since the correction unit 150 corrects the original variation curve 704 in consideration of the difference in concentration between fluorescent dyes, a test result close to the actual variation curve 706 may be obtained. Accordingly, a nucleic acid may be analyzed more accurately.

Referring back to FIG. 2, the estimation unit 160 estimates the final $C_T$s by using the fluorescent intensity variation curves corrected by the correction unit 150. Like the above-described calculation unit 120, the estimation unit 160 estimates the final $C_T$s by using a well-known calculation method for determining the threshold cycle $C_T$, e.g., first-order or second-order differentiation.

The estimation unit 160 estimates the final $C_T\_$Cal Fluor 560 by using the corrected variation curve 705 shown in FIG. 7B. According to FIG. 7B, the estimation unit 160 estimates the final $C_T\_$Cal Fluor 560 as 27.70.

Meanwhile, a process of correcting a fluorescent intensity variation curve regarding FAM dye in the correction unit 150 is as described below. The correction unit 150 corrects a crosstalk signal due to Cal Fluor 560 dye by using Equation 7, and then corrects a fluorescent intensity variation curve regarding FAM dye by using Equation 8.

Cal560_corrected flu. intensity=2plex·$a_{12}/I_{\Delta F}$

Cal560_corrected con.=Cal560_corrected flu. intensity+$\Delta C_T$ [Equation 7]

FAM_corrected=2plex−Cal560_corrected con. [Equation 8]

Figure 8A:
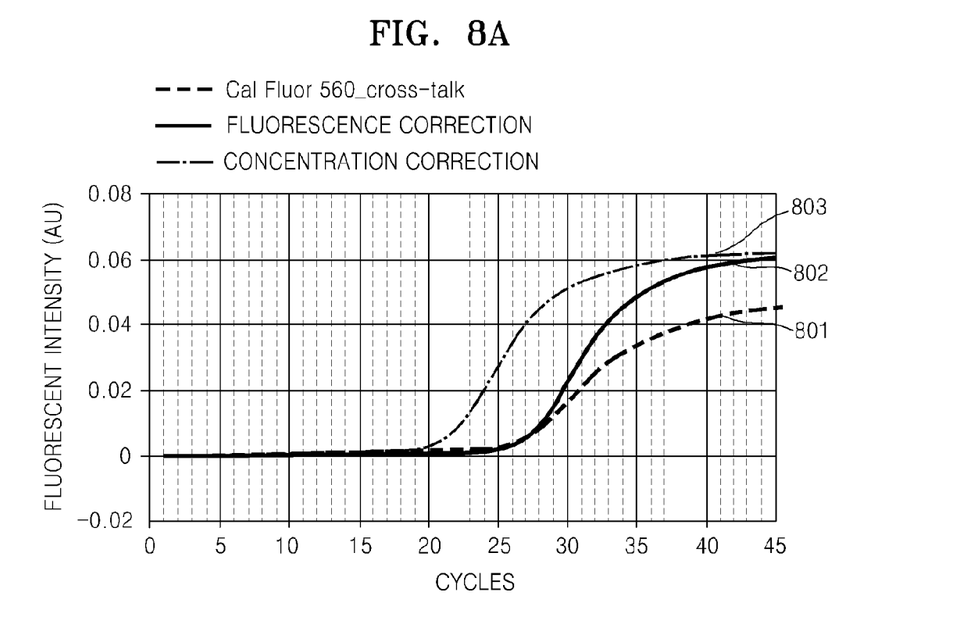
FIG. 8A is a graph showing a result of correcting a crosstalk signal due to Cal Fluor 560 dye in the correction unit.

FIG. 8A is a graph showing a result of correcting a crosstalk signal due to Cal Fluor 560 dye in the correction unit 150, according to an embodiment of the present invention. Referring to FIG. 8A, the fluorescent intensity of an original crosstalk signal 801 due to Cal Fluor 560 dye is corrected by the correction unit 150 by using Equation 7, and thus, the original crosstalk signal 801 is changed into a fluorescence-corrected crosstalk signal 802. After that, the concentration of the fluorescence-corrected crosstalk signal 802 is corrected by the correction unit 150 by using Equation 8, and thus, the fluorescence-corrected crosstalk signal 802 is changed into a concentration-corrected crosstalk signal 803.

Figure 8B:
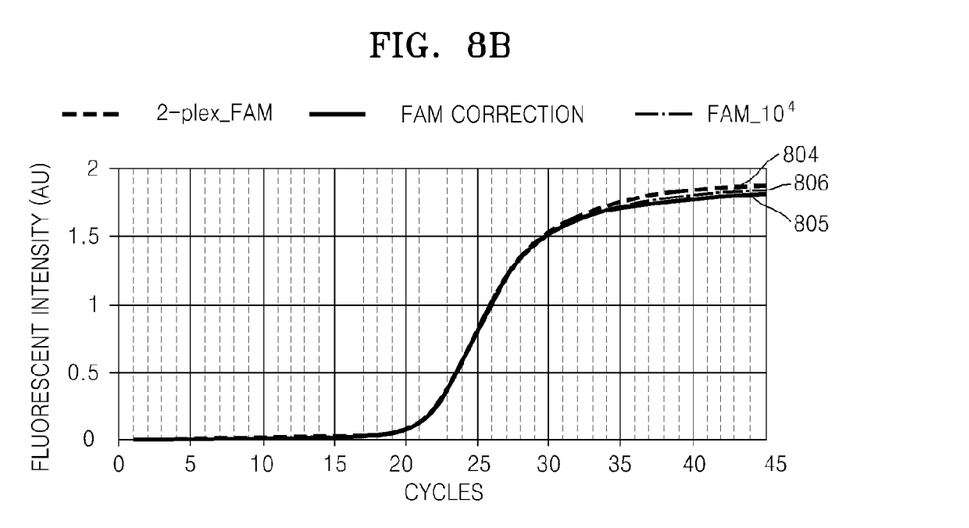
FIG. 8B is a graph showing a result of correcting a fluorescent intensity variation curve regarding FAM dye in the correction unit.

FIG. 8B is a graph showing a result of correcting a fluorescent intensity variation curve regarding FAM dye in the correction unit 150, according to an embodiment of the present invention. Referring to FIG. 8B, an original fluorescent intensity variation curve 804 regarding FAM dye is compensated for by using the corrected crosstalk signal 803 shown in FIG. 8A, and thus, is changed into a corrected variation curve 805.

As such, the corrected variation curve 805 is hardly different from an actual variation curve 806 regarding FAM dye. That is, since the correction unit 150 corrects the original variation curve 804 in consideration of the difference in concentration between fluorescent dyes, a test result close to the actual variation curve 806 may be obtained. Accordingly, a nucleic acid may be analyzed more accurately.

Referring back to FIG. 2, the estimation unit 160 estimates the final $C_T\_$FAM by using the corrected variation curve 805 shown in FIG. 8B. According to FIG. 8B, the estimation unit 160 estimates the final $C_T\_$FAM as 22.03.

According to the above-described example, the estimation unit 160 estimates the final $C_T\_$Cal Fluor 560 as 27.70 and estimates the final $C_T\_$FAM as 22.03. However, the calculation unit 120 calculates the initial $C_T\_$Cal Fluor 560 as 27.74 and also calculates the initial $C_T\_$FAM as 22.03.

When compared, the threshold cycles regarding Cal Fluor 560 are particularly different. The difference is caused by the difference in concentration between FAM dye and Cal Fluor 560 dye, and is less than the difference between the threshold cycles calculated without considering the difference in concentration.

Figure 9:
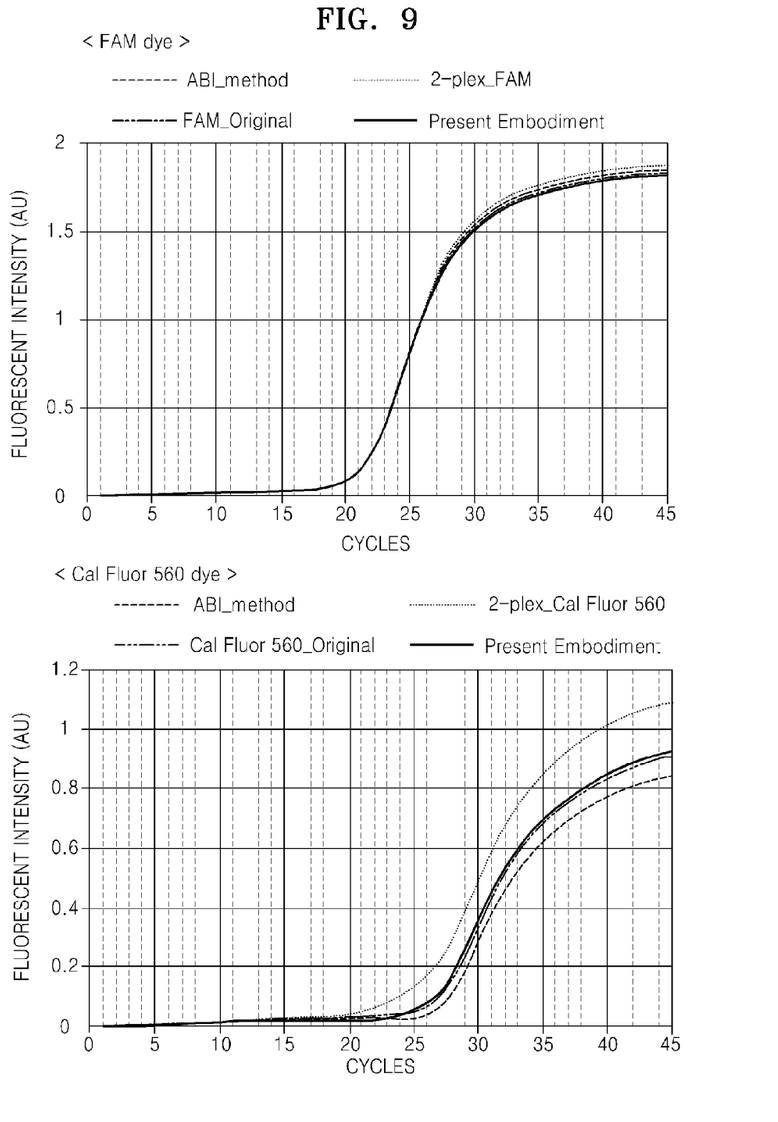
FIG. 9 is a graph showing results of analyzing multiplex (2-plex) PCR performed under the same condition in cases when the difference in concentration between fluorescent dyes is considered and is not considered.

FIG. 9 is a graph showing results of analyzing multiplex (2-plex) PCR performed under the same condition in cases when the difference in concentration between fluorescent dyes is considered and is not considered, according to an embodiment of the present invention. Referring to FIG. 9, as described above, particularly with respect to Cal Fluor 560 dye, when compared to a typical crosstalk compensation method by Applied Biosystems (U.S. Pat. No. 7,839,507), if the difference in concentration is considered according to an embodiment of the present invention, a more accurate result may be obtained.

Figure 10:
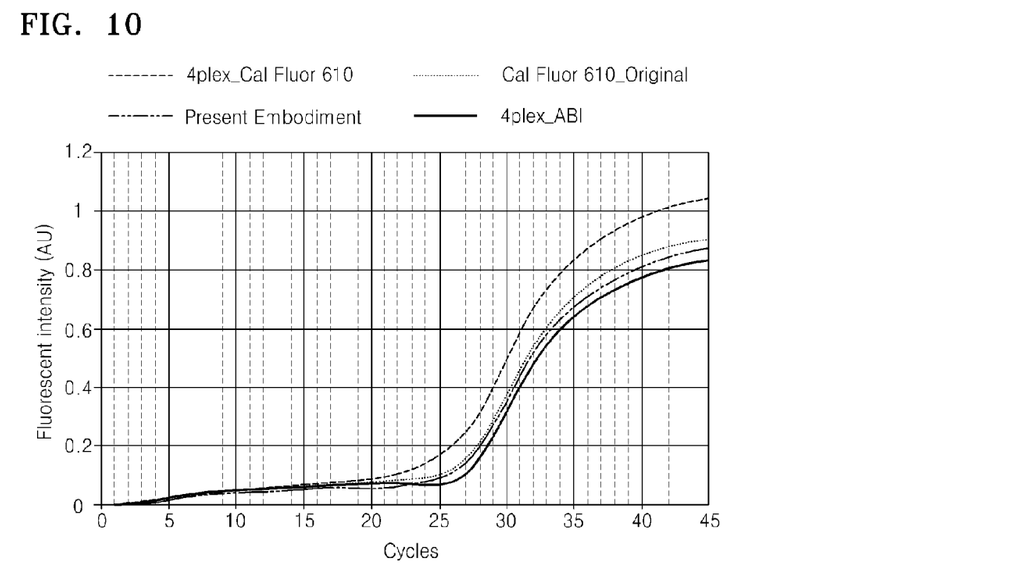
FIG. 10 is a graph showing results of analyzing multiplex (4-plex) PCR performed under the same condition in cases when the difference in concentration between fluorescent dyes is considered and is not considered.

FIG. 10 is a graph showing results of analyzing multiplex (4-plex) PCR performed under the same condition in cases when the difference in concentration between fluorescent dyes is considered and is not considered, according to an embodiment of the present invention. Referring to FIG. 10, when compared to a typical crosstalk compensation method by Applied Biosystems, if the difference in concentration is considered according to an embodiment of the present invention, a more accurate result may be obtained.

Although 4-plex PCR is not described in detail here, it would be understood by one of ordinary skill in the art that 4-plex PCR may be easily performed by using 2-plex PCR described above.

Meanwhile, the above graphs and values regarding FAM dye and Cal Fluor 560 dye are merely examples provided to promote an understanding of embodiments of the present invention, and it would be understood by one of ordinary skill in the art that the embodiments of the present invention are not limited thereto.

Figure 11:
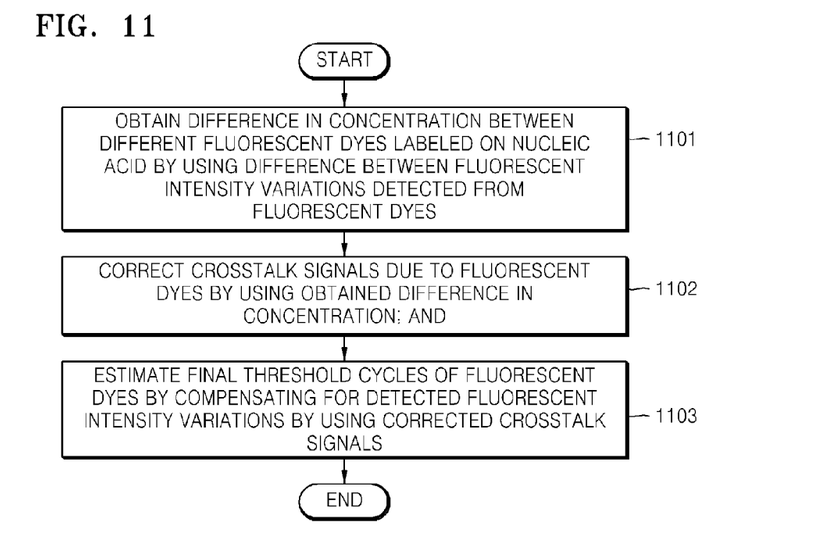
FIG. 11 is a flowchart of a nucleic acid analysis method.

FIG. 11 is a flowchart of a nucleic acid analysis method according to an embodiment of the present invention. Referring to FIG. 11, the nucleic acid analysis method includes operations performed in time series by the nucleic acid analysis apparatus 10 illustrated in FIGS. 1 and 2. Accordingly, although it is omitted here, the descriptions provided in relation to FIGS. 1 and 2 may also be applied to the nucleic acid analysis method.

In operation 1101, the concentration analysis unit 140 obtains the difference in concentration between different fluorescent dyes labeled on nucleic acid by using the difference between fluorescent intensity variation curves detected from the fluorescent dyes.

In operation 1102, the correction unit 150 corrects crosstalk signals due to the fluorescent dyes by using the obtained difference in concentration.

In operation 1103, the estimation unit 160 estimates final threshold cycles of the fluorescent dyes by compensating the detected fluorescent intensity variation curves by using the corrected crosstalk signals.

As described above, according to one or more of the above embodiments of the present invention, when a nucleic acid is analyzed by using different fluorescent dyes, since crosstalk signals may be accurately corrected by reflecting the difference in concentration between fluorescent dyes, a more accurate result of analyzing the nucleic acid may be obtained.

Meanwhile, embodiments of the present invention can be written as computer programs and can be implemented in general-use digital computers that execute the programs using a computer readable recording medium. Also, the data structure used in the embodiments of the present invention described above can be recorded on a computer readable recording medium via various means. Examples of the computer readable recording medium include information storage media (e.g., ROM, floppy disks, hard disks, etc.), optical recording media (e.g., CD-ROMs, or DVDs), etc.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nucleic acid analysis method comprising:
   detecting fluorescent intensity variations in nucleic acids labeled with fluorescent dyes;
   calculating initial threshold cycles (CTs) corresponding to each of different fluorescent dyes labeled on a nucleic acid, from fluorescent intensity variations detected from the fluorescent dyes;
   calculating a difference in concentration between the fluorescent dyes from a difference between the calculated initial $C_{TS}$;
   correcting previously stored crosstalk signals corresponding to each of the fluorescent dyes based on a fluorescent intensity correction value calculated from the calculated difference in concentration; and
   estimating final threshold cycles of the fluorescent dyes based on the corrected crosstalk signals.

2. The method of claim 1, further comprising determining whether the calculated initial threshold cycles corresponding to each of the fluorescent dyes are the same,
   wherein calculating the difference in the concentration comprises calculating the difference in concentration if it is determined that the calculated initial threshold cycles are not the same.

3. The method of claim 2, further comprising, if it is determined that the calculated initial threshold cycles are the same, estimating the final threshold cycles corresponding to each of the fluorescent dyes by compensating for the detected fluorescent-intensity variations using crosstalk correction coefficients.

4. The method of claim 1, wherein the initial threshold cycles and the final threshold cycles are values calculated by using an nth-order differentiation method ($n \geq 1$) or a threshold method,
   wherein the nth-order differentiation method comprises a method for determining a threshold cycle as a maximum value of an nth-order differentiation curve of a curve indicating the fluorescent intensity variations, and
   wherein the threshold method comprises a method for determining a threshold cycle as an x-axis value of an intersection between a threshold line parallel to an x-axis and the curve indicating the fluorescent intensity variations.

5. The method of claim 1, wherein the correcting the crosstalk signals comprises correcting the crosstalk signals by adjusting curves indicating fluorescent intensity variations of the crosstalk signals based on a difference between the fluorescent intensity correction values.

6. The method of claim 5, wherein the correcting the crosstalk signals comprises correcting the crosstalk signals by re-adjusting the adjusted curves of the crosstalk signals based on a difference between initial threshold cycles of the fluorescent dyes.

7. The method of claim 1, wherein the different fluorescent dyes are used in at least one of a multiplex polymerase chain reaction (PCR) device, a microarray, and a microfluidic device, for analyzing the nucleic acid by simultaneously detecting the fluorescent dyes.

8. The method of claim 1, further comprising measuring the fluorescent intensity variations by detecting fluorescent light emitted from the different fluorescent dyes labeled on the nucleic acid.

9. A non-transitory computer-readable recording medium having recorded thereon a computer program for executing the method of claim 1.

* * * * *